United States Patent [19]
Kroll

[11] Patent Number: 5,540,721
[45] Date of Patent: *Jul. 30, 1996

[54] PROCESS AND APPARATUS FOR DEFIBRILLATION SYSTEM WITH A SMALL CAPACITOR

[75] Inventor: Mark W. Kroll, Minnetonka, Minn.

[73] Assignee: Angeion Corporation, Plymouth, Minn.

[ * ] Notice: The term of this patent shall not extend beyond the expiration date of Pat. No. 5,342,399.

[21] Appl. No.: 339,914

[22] Filed: Nov. 15, 1994

Related U.S. Application Data

[63] Continuation of Ser. No. 989,532, Dec. 11, 1992, abandoned, which is a continuation-in-part of Ser. No. 808,722, Dec. 17, 1991, Pat. No. 5,342,399.

[51] Int. Cl.$^6$ .................................................. A61N 1/39
[52] U.S. Cl. ................................................. 607/5; 607/74
[58] Field of Search .................................. 607/2, 4, 5, 7, 607/8, 74, 68, 37, 38

[56] References Cited

U.S. PATENT DOCUMENTS

| | | | |
|---|---|---|---|
| 3,326,239 | 2/1966 | Berkovits | 128/419 D |
| 3,389,704 | 6/1968 | Buchowski et al. | 128/419 D |
| 4,168,711 | 9/1979 | Cannon et al. | |
| 4,708,145 | 11/1987 | Tacker, Jr. et al. | 128/419 D |
| 4,953,551 | 9/1990 | Mehra et al. | |
| 4,969,463 | 11/1990 | Dahl et al. | 128/419 D |
| 5,131,388 | 7/1992 | Pless et al. | 128/419 D |
| 5,199,429 | 4/1993 | Kroll et al. | 128/419 D |

FOREIGN PATENT DOCUMENTS

| | | | |
|---|---|---|---|
| 0272021 | 7/1964 | Australia | 128/419 D |
| 0280526 | 2/1988 | European Pat. Off. | |
| 286108 | 10/1983 | German Dem. Rep. | |

OTHER PUBLICATIONS

Echt, D. S. et al., Clinical Experience, Complications & Survival in 70 Patients With the Automatic Implantable Cardioverter/Defibrillator, Circulation vol. 71, No. 2, Feb. 1985.

Geddes, L. A. et al., Med. & Biol. Engng. & Computing, vol. 23, No. 2, London, Great Britian, pp. 120–130.

Lang, D. J. et al. IEEE Engng. in Medicine & Biology Society 11th Annual International Conference pp. 80–81, 1989.

Geddes et al., "Eng. and Physl. Considerations of Direct Cap. Discharge Vent. Defib.," *Med. & Biol. Engng.*, vol. 9, pp. 185–199, 1971.

Tullo et al., "Technological Improvements in Future Implantable Defibs.," *Cardio*, May 1990.

Bourland et al., "Strength–duration curves for Trap–waveforms of Various Tilts for Transchest Defib. in Animals," *Medical Instr.*, vol. 2, No. 1, 2–1978.

*Primary Examiner*—William E. Kamm
*Assistant Examiner*—Kennedy J. Schaetzle
*Attorney, Agent, or Firm*—Patterson & Keough P.A.

[57] ABSTRACT

The present invention uses the chronaxie, a characteristic time that enters into heart defibrillation. The present invention defines a figure of merit for physiologically effective current for characterizing and evaluating a defibrillation pulse. Using this figure of merit then, the present invention compares defibrillation-pulse options and to determine optima for capacitance, tilt, and pulse duration. The combined abilities of optima determination and quantitative comparison of options provides for shorter pulses and lower capacitance values than have been in common use in the prior art. The overall result of the present invention is the specifying of smaller, more efficient implantable defibrillator designs.

9 Claims, 3 Drawing Sheets

PROCESS AND APPARATUS FOR DEFIBRILLATION SYSTEM WITH A SMALL CAPACITOR

CROSS REFERENCES TO CO-PENDING PATENT APPLICATIONS

This patent application is an FWC of U.S. patent application Ser. No. 07/989,532, filed Dec. 11, 1992, now abandoned, which is a Continuation-in-part of U.S. patent application Ser. No. 07/808,722, filed Dec. 17, 1991, entitled "Small-Capacitance Defibrillation Process", now U.S. Pat. No. 5,342,399, and relates to U.S. patent application Ser. No. 07/953,485, filed Sep. 29, 1992, entitled "Short-Pulse Implantable Defibrillation System", now abandoned; U.S. patent application Ser. No. 07/835,836, filed Feb. 18, 1992, entitled "Optimal Pulse Defibrillator", now U.S. Pat. No. 5,431,686; and U.S. patent application Ser. No. 07/866,368, filed Apr. 9, 1992, entitled "Separate Capacitor Cardioversion Method for Implantable Cardioverter Defibrillators", now U.S. Pat. No. 5,334,219, all to the same assignee as the present patent application.

BACKGROUND OF THE INVENTION

1. Field of the Invention

The present invention relates generally to defibrillation processes, and more particularly to a realization that there exists an optimum capacitor value for defibrillation-pulse generation in an implantable system, a value smaller than recognized heretofore.

2. Description of the Prior Art

Defibrillation, or causing the cessation of chaotic and uncoordinated contraction of the ventricular myocardium by application of an electrical voltage and current, in its most primitive form goes back to the last century. [J. L. Prevost and F. Batelli, "Sur Quelques Effets des Deacharges Electriques sur le Couer des Mammifers, "*Comptes Rendus Hebdomadaires des Seances de L'Acadmie des Sciences*, Vol. 129, p. 1267, 1899.]

The sophistication and effectiveness of defibrillation techniques have grown rapidly in subsequent decades. One of the most recent developments has been the practical advent of implantable defibrillation systems. [R. A. Winkle, et al. "Long-term Outcome with the Implantable Cardioverter-Defibrillator," *J. Am. Coll. Cardiol.*, Vol. 13, p. 1353, 1989; M. H. Lehman and S. Saksena, "Implantable Cardioverter-Defibrillators in Cadiovascular Practice: Report of the Policy Conference of the North American Society of Pacing and Electrophysiology," *PACE*, Vol. 14 p. 107, May 1990.] With the acceptance of this technology, the new challenge is to reduce system size while preserving its effectiveness, in order to improve the patient's quality of life and to extend the range of application such systems. [R. A. Winkle, "State of the Art of the AICD," *PACE*, Vol 14, p. 961, May 1991, part II; N. G. Tullo, S. Saksena, and R. B. Krol, "Technological Improvements in Future Implantable Defibrillators," *CARDIO*, Vol. 7, p. 197, May 1990.] Until an ability to anticipate fibrillation has been achieved, it will be necessary to achieve defibrillation by passing a large current through the heart. The current must be large enough to depolarize a large fraction of the myocardium, thus extinguishing depolarization wavefronts. [D. P. Zipes, et al., "Termination of Ventricular Fibrillation in Dogs by Depolarizing a Critical Amount of Myocardium," *Am. J. Cardiol.*, Vol. 36, p. 37, July 1975.] Further, the waves must be strong enough so that the cells will not be stimulated during their vulnerable periods, causing refibrillation. [P. S. Chen, et al., "Comparison of the Defibrillation Threshold and the Upper Limit of Ventricular Vulnerability," *Circulation*, Vol 73, p. 102 May 1986.]

The high values of current that are usually employed in defibrillation procedures, and the compactness that is essential in implantable systems are conflicting requirements. For this reason, a huge premium is placed on knowledge of optimal values for various defibrillation-pulse characteristics; an optimum pulse will avoid the "waste" of current, charge, voltage, or energy, depending on which of these variables prove most relevant to successful defibrillation.

The components that dominate the physical volume of an implantable system are the capacitor and the battery, and here the avoidance of overdesign is crucial. A corollary to the proposition just stated is that accurate knowledge of which of the several defibrillation-pulse variables are dominant has an equally large premium placed upon it when an implantable defibrillator is to be designed. The present invention will address this challenge.

For reasons of simplicity and compactness, capacitor-discharge systems are almost universally used in defibrillation. Achieving the requisite electric field needed to depolarize most of the myocardial cells requires current density above a certain threshold value, and via Ohm's law, this means the process is favored by achieving sufficiently low electrical resistance in the discharge path. For this reason, the use of electrodes of relatively large surface area has for a long time been the norm. [A. C. Guyton and J. Satterfield, "Factors Concerned in Defibrillation of the Heart, Particularly through the Unopened Chest," *Am. J. of Physiology*, Vol. 167, p. 81, 1951.] The discharge of a capacitor C through a fixed resistance R results in a voltage-versus-time curve (and hence, current versus time as well) that is a declining exponential function, with a characteristic time given by the product RC. But, it has also been recognized for some time that the low-voltage (and low-current) "tail" of the capacitor-discharge pulse is detrimental. [J. C. Schuder, G. A. Rahmoeller, and H. Stoeckle, "Transthoracic Ventricular Defibrillation with Triangular and Trapezoidal Waveforms, " *Circ. Res.*, Vol. 19, p. 689, October 1966; W. A. Tacker, et al., "Optimum Current Duration for Capacitor-discharge Defibrillation of Canine Ventricles," *J. Applied Physiology*, Vol. 27, p. 480, October, 1969.] The exact reason for this detrimental effect is not known, although plausible speculations exist.

Efforts to deliver a more nearly rectangular pulse over thirty years ago employed a series inductor in the discharge path, and improved results over the simple RC discharge were noted. [R. S. MacKay and S. E. Leeds, "Physiological Effects of Condenser Discharges with Application to Tissue Stimulation and Ventricular Defibrillation," *J. Applied Physiology*, Vol 6, p. 76, July 1953; W. B. Kouwenhoven and W. R. Milnor, "Treatment of Ventricular Fibrillation Using a Capacitor Discharge," *J. Applied Physiology*, Vol. 7, P. 253 November 1957.] Subsequent further efforts in the same direction used RLC (resistor-inductor-capacitor) delay lines, and reported further improvement. [R. C. Balagot, et al, "A Monopulse DC Defibrillator for Ventricular Defibrillation," *J. Thoracic and Cardiovascular Surgery*, Vol. 47, p. 487, April 1964.] But unfortunately, inductors are bulky components that are unattractive for incorporation in defibrillator systems, especially in implantable systems. For this reason, most efforts have been directed at time-truncated capacitor discharges. [J. C. Schuder, et al. "Transthoracic Ventricular Defibrillation in the Dog with Truncated and Untruncated Exponential Stimuli," *IEEE Trans. Biom. Eng.*, Vol. BME- 18, p. 410, November 1971.] That is, the capacitor discharge is simply interrupted by opening a switch at some middle point, typically, at about the time that the characteristic "RC time" has been reached, with a result approximating that of the example illustrated in FIG. 1. The advent of compact solid-state switches has made such pulse tailoring a straight-forward matter.

The well-known waveform in FIG. 1 has for a long time been termed a monophasic pulse. It is generated by charging a capacitor from a high-voltage power supply which isolated from the capacitor by a rectifier, as illustrated in FIG. 2; then a switch in series between capacitor and heart is simply closed to initiate the pulse, and opened to terminate (or truncate) the monophasic pulse.

The amount of voltage decline (and current decline, assuming the heart to constitute a linear resistor) that has occurred at the time of pulse termination relative to the initial voltage, is termed the tilt of the pulse. In algebraic language, $$\text{tilt} = (V_{initial} - V_{final})/V_{initial}. \qquad \text{Eq. 1}$$

Since the amplitude declines in one characteristic time to 1/e of its initial value, where e is the base of the Napierian system of logarithms, the tilt of a pulse terminated at the RC time is about 0.63, or 63%, to use the customary description. Typical values employed in monophasic defibrillation fall in the range from 60% to 70%. An example having a 67% tilt is shown in FIG. 3.

A waveform that is known equally well is the biphasic waveform, illustrated in FIG. 4. To create this kind of defibrillation pulse, the series switch is eliminated and a reversing switch that has long been used in the electronic art is employed instead. It consists of four switches in an "H" configuration, as illustrated in FIG. 5. Switches S1 and S4 are closed simultaneously to initiate the first phase of the waveform; to end the first phase these two switches are opened and simultaneously, the switches S2 and S3 are closed, creating a path for current to flow in the opposite direction from the capacitor through the heart. Opening all four switches terminates the second phase of the biphasic defibrillation shock.

The many studies that have been published on optional defibrillation-pulse properties have tended to focus on the energy stored in the capacitor, or charge times voltage. But with the truncation of the pulse, this total energy is unrelated to the energy delivered to the heart unless a number of other variable values are specified. Furthermore, in conventional systems, the residual charge stored in the capacitor is not recovered. Thus if one's aim, as at present, is to minimize the size and volume of an implantable defibrillation system, total stored energy is not a very useful criterion. Far more relevant is optimal capacitance. And given a particular value for the heart's resistance, with 50 ohms being a representative value for electrodes of typical design, then the amount of tilt is uniquely related to capacitance for a given pulse duration, and becomes an equally meaningful quantity. Finally, the pulse-duration optimum needs careful study.

Exhaustive scrutiny of published data in the literature shows that the prior art offers no determinations of optimal tilt or pulse duration for a capacitor of a particular size, nor does it offer any attempt to define an optimal value of capacitance for an implantable defibrillator. But the literature does offer a rich fund of data on defibrillation-pulse effectiveness presented in a way that permits a determination of the associated tilts and pulse durations used by those researchers. Furthermore, an extension of well-accepted physiological models results in a model that predicts optimal tilt and pulse duration for an arbitrary capacitance.

The present invention predicts the optimal capacitance for an implantable defibrillator.

SUMMARY OF THE INVENTION

The pioneer physiologist L. Lapicque collected substantial amounts of data on the amount of current required for tissue stimulation, using constant-current pulses of various durations. [L. Lapicque, "Definition Experimentelle de l'excitabilite," *Proc. Soc. de Biol.*, Vol. 77, p. 280, 1909.] He established an empirical relationship between the current I and the pulse duration $d_p$, having the form $$I = K_1 + (K_2/d_p). \qquad \text{Eq. 2}$$

Thus the necessary current and the pulse duration are related by a simple hyperbola, shifted away from the origin by the amount of the constant term $K_1$. Multiplying this expression through by $d_p$ yields an expression in charge, rather than current, and constitutes an earlier and consistent equation given by Weiss. [G. Weiss, "Sur la Possibilite de Rendre Comparable entre Eux les Appareils Suivant a l'Excitation Electrique," *Arch. Ital. de Biol.*, Vol. 35, p. 413, 1901.]) Thus, the stimulating current required in a pulse of infinite duration is $K_1$, a current value Lapicque termed the rheobase. Shortening the pulse required progressively more current, and the pulse length that required a doubling of current for excitation, or $2K_1$, he termed the chronaxie, $d_c$. Substituting $2K_1$ and $d_c$ into Eq. 2 in place of I and $d_p$, respectively, thus yields $$d_c = K_2/K_1. \qquad \text{Eq. 3}$$

Lapicque's model described cell stimulation, rather than defibrillation, but Bourland, et al., demonstrated that defibrillation thresholds in dogs and ponies exhibited the same functional dependence as in the Lapicque model, provided average current is used in the exercise. [J. D. Bourland, W. Tacker, and L. A. Geddes, "Strength-Duration Curves for Trapezoidal Waveforms of Various Tilts for Transchest Defibrillation in Animals", *Med. Instr.*, Vol 12, p. 38, 1978.] In a companion paper, the same workers showed that average current is a useful and consistent measure of defibrillation effectiveness for time-truncated pulses of a given duration through a substantial range of durations, from 2 to 20 milliseconds; in other words, so long as the exponential "tail" is eliminated, average current and pulse duration adhere qualitatively to the Lapicque function. [J. D. Bourland, W. Tacker, and L. A. Geddes, "Comparative Efficacy of Damped Sine Waves and Square Wave Current for Transchest Defibrillation in Animals," *Med Instr.*, Vol 12, p. 38, 1978.] From the observations made by Bourland and co-workers, the inventors have inferred a heart chronaxie time of 3.6 milliseconds.

To the data of Bourland, the inventors have added values taken from the work of Wessale, et al., on dogs, and Jones, et al., on chicks, both of which groups gave curves of current value versus pulse duration, and these both yielded chronaxie times of 1.8 milliseconds. Further, it has been possible to calculate chronaxie time from data published by Gold (calf, 2.7 milliseconds), Niebauer (dog, 4.1 milliseconds), Feeser (dog, 2.0 milliseconds), and Geddes (dog, averaged from curves for pulses of different tilts, 2.8 milliseconds). This synopsis yields an average chronaxie time of 2.7 milliseconds, and a median value of 2.7 milliseconds also. All of this work is relatively recent, being clustered in the time period from 1977 to 1990. An example of Lapicque's translated hyperbola, sometimes termed a "strength-duration" curve is plotted in FIG. 6. This particular curve is based explicitly on the values of average current and pulse duration inferred from the literature in the manner just described. Note that at the chronaxie time of 2.7 milliseconds, the current required for defibrillation is by definition of the chronaxie, just twice the rheobase current. For a longer pulse, the average current required is smaller. To convert this curve into a "universal curve," it would be necessary to convert ordinate calibration from current to current density, but data from the literature are not sufficiently detailed to permit such a conversion. If such data were available, they would define a rheobase current density having a fundamental meaning as fundamental as that of chronaxie time.

The present invention is an analytic method for essaying waveform optimization. It builds upon the models of Lapicque and Weiss, and the findings of Bourland, et al. Taking advantage of the last group's discovery that average current, $I_{ave}$, is meaningful, one can apply their discovery to the truncated capacitor-discharge waveform, writing with the help of Eqs. 2 and 3, $$I_{ave} = [K_1(1 + d_c/d_p)].  \quad \text{Eq. 4}$$

Solving for rheobase current yields $$K_1 = [I_{ave}/(1 + d_c/d_p)].  \quad \text{Eq. 5}$$

Treating the right-hand side of this expression as a waveform-dependent effective current, the challenge, then, is to maximize this effective current while manipulating the variables describing a practical defibrillation system, variables drawn from a set including capacitance, resistance, tilt, initial voltage, average current, and stored charge. The earlier application for which the present invention is a continuation-in-part [Ser. No. 07/808,722] and also a second co-pending patent application use the term physiologically effective current, $I_{pe}$, in place of the term effective current, and that practice is continued here. Thus the object is to maximize the expression $$I_{pe} = [I_{ave}/(1 + d_c/d_p)].  \quad \text{Eq. 6}$$

In the first co-pending application, it is shown that the relationship of the physiologically effective current to several relevant variables can be written $$I_{pe} = [I_{ave}d/(d_c + d_p)] = [(\text{delivered charge})/(d_c + d_p)] = CV_i(\text{tilt ratio})/(d_c + d_p).  \quad \text{Eq. 7}$$

The process of maximization is shown to yield for optimal pulse duration $$d_p = (RC + d_c)/(e - 1),  \quad \text{Eq. 8}$$

which amounts approximately to the average of the system time constant and the heart-tissue (chronaxie) time constant.

Further analysis in terms of physiologically effective current suggests the nonobvious proposition that there also exists a capacitance optimum, a value that is independent of energy stored; the stored energy can of course be altered by varying voltage, but doing so does not alter the best choice of capacitance. To determine optimal capacitance, one writes an expression for $I_{pe}$ as a function of E, R, C, and $d_c$, and differentiates it with respect to C. Energy appears only as a factor, and drops out when the expression is equated to zero to find the extremum of the transcendental expression. The result, numerically determined, is $$C = (0.8 \, d_c)/R.  \quad \text{Eq. 9}$$

This expression further emphasizes that the RC product associated with the pulse must approximate the chronaxie time, $d_c$. Assuming the chronaxie time of 2.7 milliseconds cited before, and the typical interelectrode resistance of 50 ohms, one finds an optimal capacitance value of 43 microfarads.

Having a most favorable value of capacitance much lower than that typically employed, 140 microfarads, of course has significant ramifications. This provides a size reduction and performance enhancement at the same time. In two cases other workers have used capacitance values in the neighborhood of 50 microfarads, but as an incidental matter while focusing on their primary interest in studying the effectiveness of pulse sequences. The potential intrinsic benefit of the smaller capacitor went unnoted in both cases. An animal study used 50 microfarads specifically. [M.-S. Chang, et al., "Double and Triple Sequential Shocks Reduce Ventricular Defibrillation Threshold in Dogs With and Without Myocardial Infarction," *JACC*, Vol. 8, p. 1393.] In a contemporaneous human study, capacitance is not cited, but can be inferred to lie in the range from 40 to 50 microfarads. [D. L. Jones, et al., "Internal Cardiac Defibrillation in Man: Pronounced Improvement with Sequential Pulse Delivery in Two Different Lead Orientations," *Circulation*, Vol. 73, p. 484, March 1986.]

An extension of the analysis given above permits determination of optimal tilt, as plotted in FIG. 7. It is given (as a decimal fraction and not a percentage) by the expression $$\text{tilt} = 1 - \exp(-d_p/RC),  \quad \text{Eq. 10}$$

where the pulse duration $d_p$ is given by Eq. 8. For the numbers and there (2.7 milliseconds, 50 ohms, and 43 microfarads) it amounts to about 72%. But, if other factors dictate changes in capacitance value, then optimal tilt also changes. For example, at 100 microfarads, tilt should be about 58%, and at 250 microfarads, about 50%.

Knowledge of optimal values makes it possible to effect performance and efficiency improvements. For example, present technology typically employs a 140-microfarad capacitor charged to 750 volts, and an associated energy storage of 39.4 joules. Although energy stored is not simply related to the defibrillation effectiveness of a system, it remains a crucial design factor because it is proportional to the physical volume of the capacitor. The physiologically effective current for such a system is $I_{pe} = 6.79$ amperes. Now return to the capacitor value of 43 microfarads and tilt of 72%. The same value of $I_{pe}$ could be delivered with a stored energy of only 30.7 joules and an initial voltage of 1195 volts. In other words, the conventional design requires 28% more energy, and hence 28% more volume, to meet the figure of merit achieved in the system of the present invention. It might well require higher battery volume as well, although additional factors can affect that determination.

It must be conceded that voltages near and above 1000 volts are troublesome with present-day electronic switches, but compromise is possible. For example, an 85-microfarad capacitor charged to 878 volts, and discharged for a tilt of 61% will provide the same $I_{pe}$ as before, but do so with a stored energy of only 32.8 joules. In this compromise case, the conventional system requires over 20% more energy storage and hence 20% more capacitor volume than does the new design.

At the present state of the art, the capacitor technology yielding the highest energy density is that of the double-anode, etched-foil aluminum capacitor. These have a rating of 375 volts in pulse applications. Two such capacitors, each of 178 microfarads and placed in series, will provide 85 microfarads chargeable to 750 volts, for an $I_{pe}$ of 5.8 amperes, and a required storage of only 24 joules. With the conventional 140-microfarad capacitor charged to 640 volts and discharged to a 65% tilt, a total storage of 28.7 joules is necessary. Hence once again, the conventional system requires over 20% more energy storage and 20% more capacitor volume than does the new design.

In general, the new options in design involve reducing pulse duration to approach more nearly the heart's chronaxie time, thus increasing effective current, or reducing pulse duration and capacitor value to reduce device size. This is in contrast to the conventional design strategy of boosting capacitor value in order to produce "high-energy-output" systems that may marginally improve defibrillation effectiveness, while at the same time boosting system volume and size as well. Numerous studies have demonstrated that stored energy and pulse energy are at best, insufficient measures of effectiveness. [C. F. Babbs and S. J. Whistler, "Evaluation of the Operating Internal Resistance, Inductance, and Capacitance of Intact Damped-Sine-Wave Defibrillators," *Medical Instrum.*, Vol. 12, p. 34, January–February 1978.] Furthermore, pulses of greater-than-optimal duration are at best wasteful, and at worst, detrimental.

The analytical findings that are the basis of the present invention can be summarized as follows:

1. The optimal value of defibrillation capacitance is relatively constant, being a function only of the chronaxie and the interelectrode resistance. It is not determined by any stored-energy or delivered-energy limitation or requirement.
2. The optimal tilt is in turn a function of capacitance, and ranges from 50% to essentially 100%.
3. The optimal pulse duration for a given capacitance value is a compromise between the heart's chronaxie time and the RC time of the system, where R is interelectrode resistance and C is the value of the defibrillation capacitor. Thus this optimal duration is not a constant.
4. Since chronaxie times are typically in the 2-to-4-millisecond range, and the durations recommended here exceed the chronaxie time, these recommendations fall in a safe range; it has been shown that pulses 2 milliseconds or less in duration either do not defibrillate, or do not restore normal function in a reasonable time. [L. A. Geddes and W. A. Tacker, "Engineering and Physiological Considerations of Direct Capacitor-Discharge Ventricular Defibrillation," *Med. Biol. Eng.*, Vol. 9, p. 185, 1971.]
5. Rather than maximizing energy for effective defibrillation, one should maximize physiologically effective current while minimizing the energy required to achieve a given effective-current level, this to minimize myocardial damage. [P. A. Rubio and E. M. Farrell, "Low-Energy Direct Defibrillation of the Human Heart," *Ann. Thoracic Surgery*, Vol. 27(1), p. 32, January 1978; C. F. Dahl, et al., "Myocardial Necrosis from Direct Current Countershock: Effect of Paddle Electrode Size and Time Interval between Discharges," *Circulation*, Vol. 50, p. 956, November 1974.]

Significant aspects and features of the present invention include the use of a defibrillation capacitor having an equivalent value of under 120 microfarads.

Another significant aspect and feature of the present invention is a reduction of capacitor volume and hence system volume for a given degree of defibrillation effectiveness.

Still another significant aspect and feature of the present invention is an increase in of defibrillation effectiveness for a given system volume.

Yet another significant aspect and feature of the present invention is the determination of an optimal capacitance value.

A further significant aspect and feature of the present invention is the determination of an optimal tilt.

A still further significant aspect and feature of the present invention is a tilt in the range from 40% to 90%.

An additional significant aspect and feature of the present invention is the use of electrolytic capacitors optionally in series or in parallel to yield effective capacitance values of under 120 microfarads.

A still additional significant aspect and feature of the present invention is the use of electrolytic capacitors and voltages under 1000 volts.

One other significant aspect and feature of the present invention is the use of film capacitors having effective capacitance values in the range from 35 to 65 microfarads.

Still one other significant aspect and feature of the present invention is the use of film capacitors and voltages between 800 and 1200 volts.

Having thus described embodiments and features of the present invention, it is a principal object of the invention to use a defibrillation capacitor having an equivalent value of under 120 microfarads.

One object of the invention is a reduction of capacitor volume and hence system volume for a given degree of defibrillation effectiveness.

Another further object of the invention is an increase of defibrillation effectiveness for a given system volume.

A further object of the invention is the determination of an optimal capacitance value.

Still another object of the invention is the determination of an optimal tilt.

A still further object of the invention is the use of electrolytic capacitors optionally in series or in parallel to yield equivalent capacitance values of under 120 microfarads.

An additional object of the invention is the use of electrolytic capacitors and voltages under 1000 volts.

Yet an additional object of the invention is the use of film capacitors having effective capacitance values in the range from 35 to 65 microfarads.

A still additional object of the present invention is the use of film capacitors and voltages between 800 and 1200 volts.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
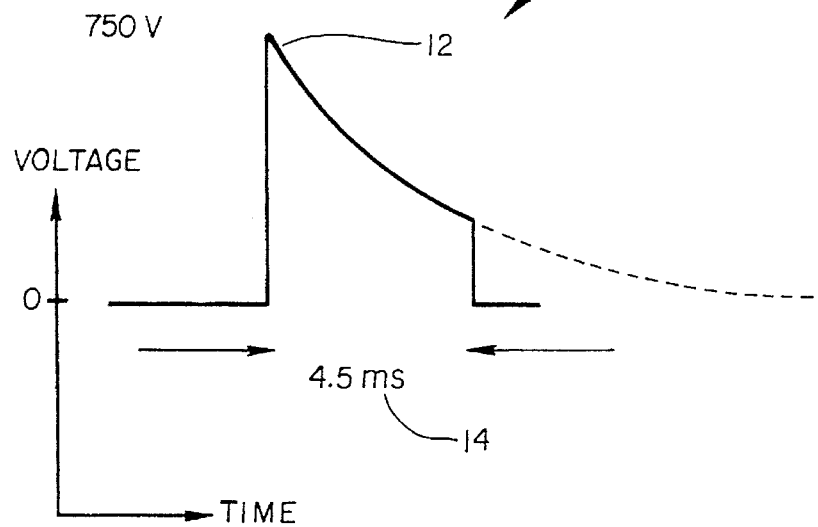
FIG. 1 illustrates a monophasic pulse of the prior art achieved by truncating a capacitor-discharge pulse.

FIG. 1 illustrates a waveform 10, constituting a monophasic pulse for defibrillation, which for a given capacitor and discharge-path resistance is fully specified by means of citing an initial voltage 12 of a predetermined duration 14.

Figure 2:
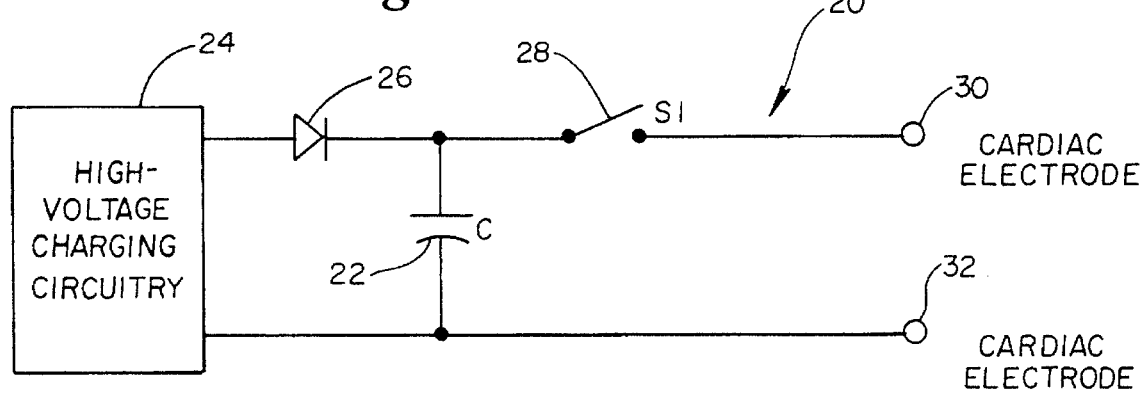
FIG. 2 illustrates a circuit of the prior art used for generating a monophasic pulse.

FIG. 2 illustrates a circuit 20 of the prior art for generating the monophasic waveform of FIG. 1, including a capacitor 22 charged from the high-voltage power supply 24 through the rectifier 26, the rectifier preventing discharge of the capacitor 22 until the switch 28, positioned between the capacitor 22 and the cardiac electrodes 30 and 32, is closed, thus initiating the monophasic pulse; opening the switch 28 terminates (or truncates) the monophasic pulse.

Figure 3:
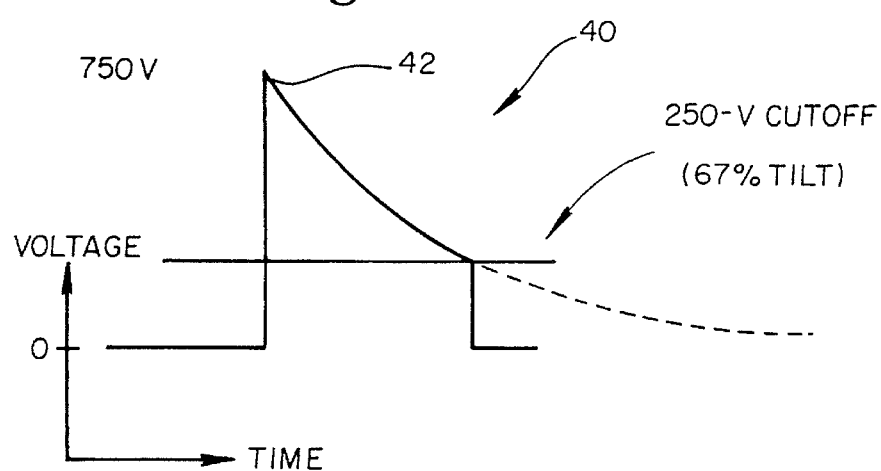
FIG. 3 illustrates a monophasic pulse of the prior art having a tilt of 67%.

FIG. 3 illustrates a waveform 40, constituting a monophasic pulse for defibrillation, which for a given capacitor and discharge-path resistance is fully specified by means of citing initial voltage 42, chosen here to be 750 volts, and tilt 44, which is voltage decline, chosen here to be 500 volts, during the pulse duration as compared to the initial voltage 42, and hence constituting a tilt of 67% in this example.

Figure 4:
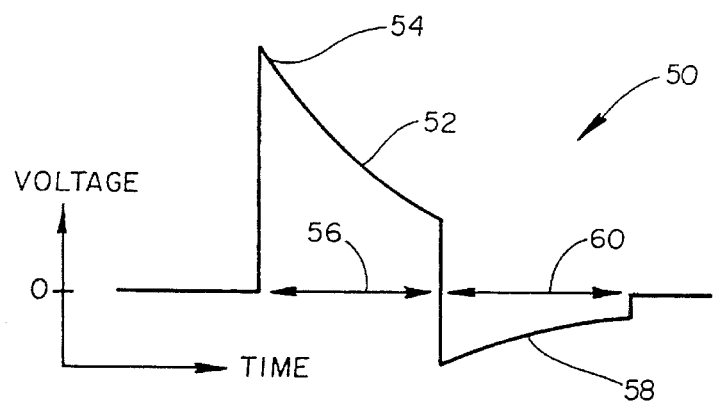
FIG. 4 illustrates a biphasic pulse of the prior art.

FIG. 4 illustrates a waveform 50, constituting a biphasic pulse for defibrillation, in which for a given capacitor and discharge-path resistance the first phase 52 is fully specified by means of citing initial voltage 54 and first-phase duration 56, and the second phase 58 is fully specified by citing second-phase duration 60.

Figure 5:
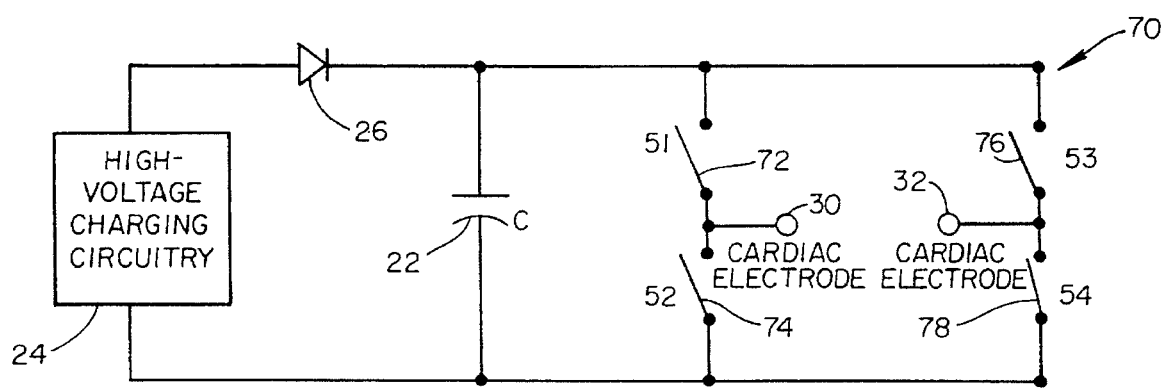
FIG. 5 illustrates a circuit of the prior art used for generating a biphasic pulse.

FIG. 5 illustrates a circuit 70 of the prior art for generating the biphasic waveform of FIG. 4, including a capacitor 22 charged from the high-voltage power supply 24 through the rectifier 26, the rectifier preventing discharge of the capacitor 22 until the switches 72, 74, 76, and 78 are operated. In the operating sequence, switches 72 and 78 are first closed to provide paths to the cardiac electrodes 30 and 32 and hence through the heart in a first direction that constitutes the first phase of the biphasic waveform 50. Second, the switches 72 and 78 are opened to terminate the first phase of the biphasic waveform 50 and the switches 74 and 76 are simultaneously closed to initiate the second phase of the biphasic waveform 50. And third, the switches 74 and 76 are opened to terminate the second phase of the biphasic waveform 50.

Figure 6:
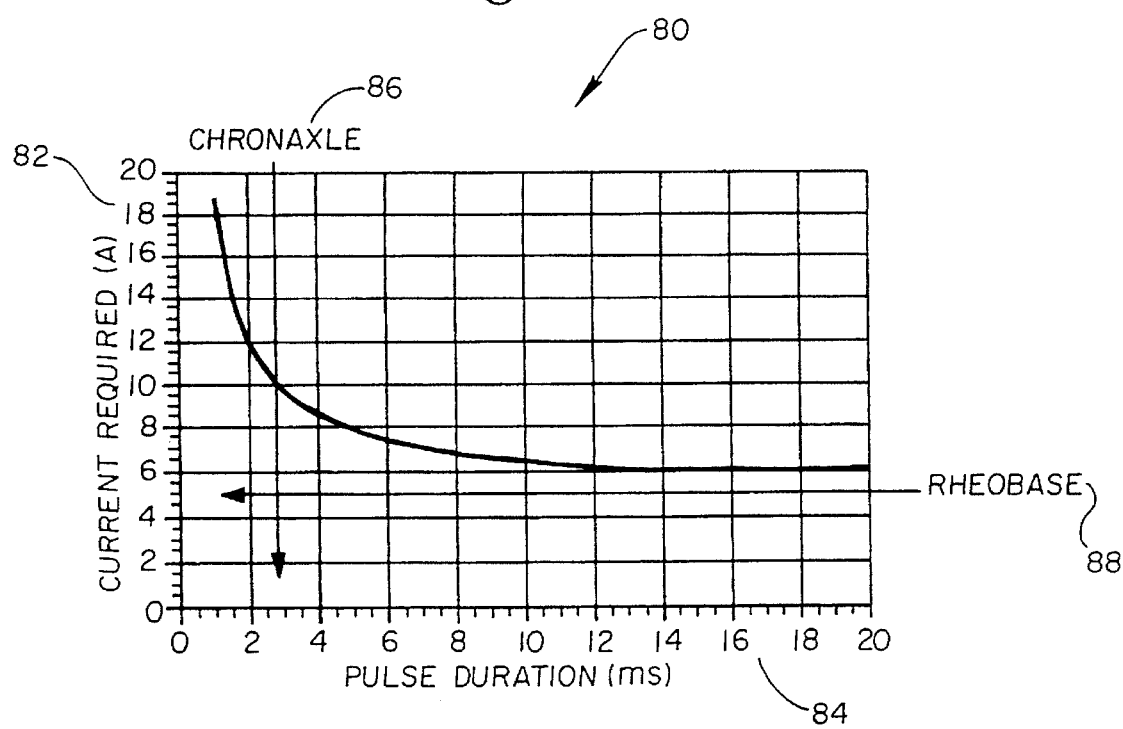
FIG. 6 illustrates a "strength-duration" curve of the present invention plotting current required for defibrillation versus pulse duration, and as defined by equation 2; and, FIG. 7 illustrates a curve of the present invention plotting optimal tilt versus capacitance.

FIG. 6 illustrates a strength-duration curve 80 of the present invention based upon extensive data extracted from the literature, which relates average current required for defibrillation plotted against the ordinate 82 to the pulse duration plotted against the abcissa 84. Prominently displayed are the chronaxie 86, a basic cardiac characteristic time, and the rheobase 88, a characteristic current that is equally fundamental once current geometry has been specified.

Figure 7:
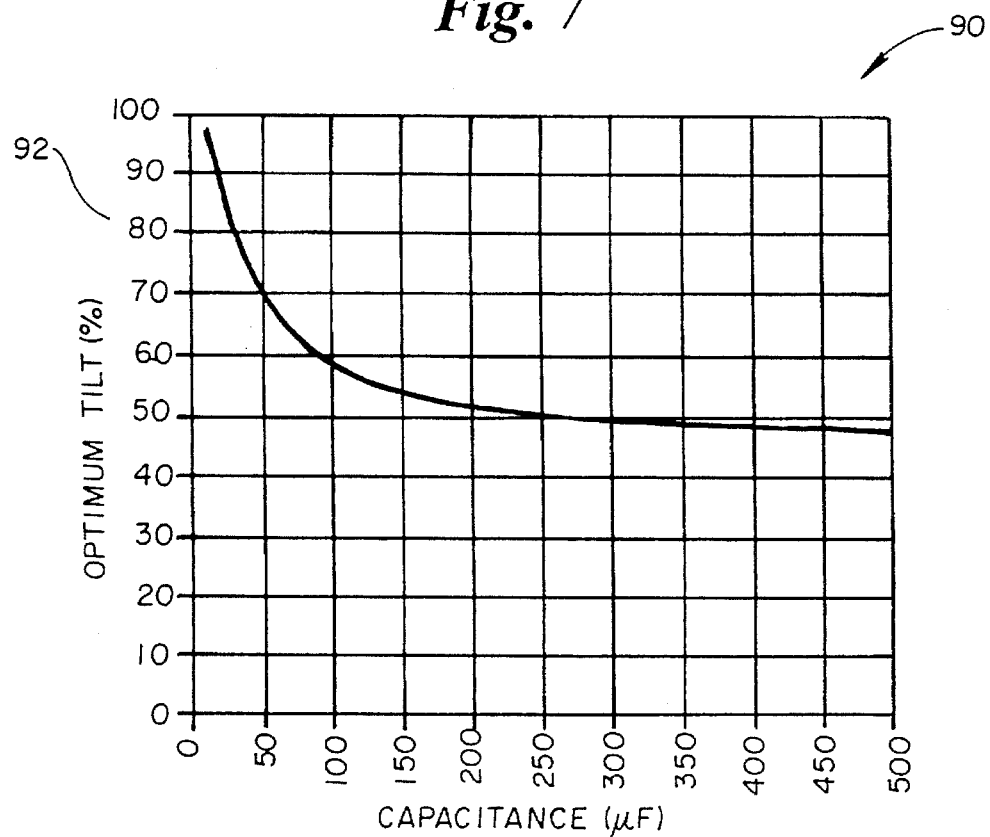

FIG. 7 illustrates a tilt-versus-capacitance curve 90 of the present invention, based upon calculations of optima as described in Eqs. 2 through 10, which relates optimal tilt of a defibrillation pulse plotted against the ordinate 92 to the capacitance employed, the value of which is plotted against the abcissa 94. For the small capacitance values favored in the present invention, less than 120 microfarads, tilts greater that 56% are favored.

MODE OF OPERATION

The present invention uses the chronaxie, a characteristic time that enters into heart defibrillation, that is defined by applying the model of L. Lapicque to the defibrillation problem. In accordance with the teachings of the present invention, a figure of merit is defined as the physiologically effective current for characterizing and evaluating a defibrillation pulse. This figure of merit then further provides a comparison of defibrillation-pulse options and determines optima for capacitance, tilt, and pulse duration as illustrated in FIGS. 6 and 7. The combined abilities of optima determination and quantitative comparison of options then guides the inventors to invoke shorter pulses and lower capacitance values than have been in common use. The overall result of this is the specifying of smaller, more efficient implantable defibrillator designs than have been possible heretofore.

The experimental findings which are the basis of one aspect of the present invention are summarized as follows:

1. The use of a smaller capacitor to generate a monophasic waveform significantly lowers defibrillation energy requirements. In a canine study, the stored energy and delivered energy required for defibrillation were compared for the use of both a 140 microfarad and 85 microfarad capacitor. The use of the 85 microfarad capacitor reduced the stored energy requirement from 6.5 to 5.9 Joules. The delivered energy was reduced from 5.9 to 5.1 Joules, on average.

2. The use of a small capacitor to generate a biphasic waveform significantly lowers energy requirements. This was tested in a porcine model with capacitors of 140 and 85 microfarad. The 85 microfarad capacitor reduced the stored energy requirement from 7.5 to 5.9 Joules. The delivered energy requirement was reduced from 7.4 to 5.9 Joules.

3. The use of a smaller capacitor lowers the impedance for the defibrillation pulse. This appears to be due to two factors. The first factor is that the small capacitor delivers a shorter duration pulse. That results in higher frequency components in the pulse. There is a capacitive effect in the electrode-electrolyte interface known as the Helmholtz double-layered capacitor. The higher frequency components couple better across this capacitor, and thus, lower the impedance. The second factor for the decreased impedance is voltage related. For a given amount of energy, the smaller capacitor must be charged to a higher voltage. The impedance at the electrode-electrolyte interface and of the myocardium itself appears to be lowered by increased voltages. This is probably due to increased activations at the electrode interface. Thus, because of their slightly higher voltage, small capacitor waveforms will feature a lower impedance.

This impedance lowering effect is one of the significant aspects of the present invention. There is a synergy between this lowered impedance, caused by the smaller capacitor, and the improved cardiac utilization of the pulse which is caused by the pulse duration being closer to the chronaxie time. These two factors, among other factors, work together to increase the efficiency of the small capacitor waveform.

In the canine study of the monophasic wave, the impedance was lowered from an average of 57.3 ohms to an average of 53.9 ohms when going from the 140 to the 85 microfarad capacitor.

Various modifications can be made to the present invention without departing from the apparent scope hereof. The capacitors can be combined in parallel and (or) series to achieve the desired capacitance. The defibrillation can be accomplished through various combinations of electrodes, including but not restricted to patch, subcutaneous, housing, and the several kinds of cardiac-catheter electrodes.

I claim:

1. An improved implantable defibrillator system for producing a truncated capacitor-discharge biphasic-waveform output defibrillation pulse, the implantable defibrillator system being a self-contained human implantable device including a pulse-generating capacitor means for storing an electrical charge, means for internally charging the pulse-generating capacitor means, and means for selectively discharging the electrical charge in the pulse-generating capacitor means through electrodes implanted in a human patient in response to a means for sensing of a myocardial fibrillation in the human patient, the improvement comprising:

the pulse-generating capacitor means having an equivalent capacitance value of less than 120 microfarads.

2. The system of claim 1 wherein the capacitor means stores a maximum electrical energy of less than 30 joules.

3. The system of claim 1 wherein the capacitor means has a maximum initial charge value that is less than 1000 volts.

4. The system of claim 1 wherein the means for selectively discharging the electrical charge limits the defibrillation pulse to a duration that is smaller than 5 milliseconds.

5. The system of claim 1 wherein the pulse-discharge capacitor means is comprised of at least one electrolytic capacitor.

6. The system of claim 1 wherein the means for selectively discharging the electrical charge produces a tilt value in a first phase of the biphasic waveform is in a range from 40% to 90%.

7. A method for selecting an optimal capacitance value for an implantable defibrillator system that produces a truncated capacitor-discharge biphasic-waveform output defibrillation pulse, the implantable defibrillator system being a self-contained human implantable device including a pulse-generating capacitor for storing an electrical charge, a battery for internally charging the pulse-generating capacitor, and a controller for selectively discharging the electrical charge in the pulse-generating capacitor through electrodes implanted in a human patient in response to a sensing of a myocardial fibrillation in the human patient, the method comprising the steps of:

(a) determining an equivalent capacitance value for one or more charge steerage devices that comprise the pulse-generating capacitor means; and (b) selecting capacitance values for the one or more charge storage devices such that the pulse-generating capacitor means has an optimal capacitance that is the equivalent capacitance value and is less than 120 microfarads.

8. The method of claim 7 wherein step (b) is accomplished by performing the steps of:

(b1) determining a maximum electrical energy rating of the capacitor means;

(b2) determining a physiologically effective current for a defibrillation pulse delivered by the implantable defibrillator system for a range of capacitance values; and (b3) selecting a capacitance value among the range of capacitance values that maximizes the physiologically effective current for the maximum electrical energy rating of the capacitor means.

9. The method of claim 7 wherein step (b) is accomplished by performing the steps of:

(b1) determining a desired physiologically effective current for a defibrillation pulse delivered by the implantable defibrillator system; and (b2) minimizing the electrical energy of the electrical charge that is required to be stored in the pulse-generating capacitor means in order to deliver the defibrillation pulse having the desired physiologically effective current.

* * * * *